United States Patent [19]

Papenfuhs

[11] Patent Number: 6,057,464
[45] Date of Patent: May 2, 2000

[54] SULPHATES OF FATTY-ACID POLYHYDROXYALKYLAMIDES AND THEIR USE

[75] Inventor: Bernd Papenfuhs, Obertshausen, Germany

[73] Assignee: Clariant GmbH, Frankfurt, Germany

[21] Appl. No.: 09/214,212

[22] PCT Filed: Jun. 21, 1997

[86] PCT No.: PCT/EP97/03266

§ 371 Date: Dec. 23, 1998

§ 102(e) Date: Dec. 23, 1998

[87] PCT Pub. No.: WO97/49678

PCT Pub. Date: Dec. 31, 1997

[30] Foreign Application Priority Data

Jun. 27, 1996 [DE] Germany .............. 196 25 711

[51] Int. Cl.⁷ .............................................. C07C 233/50
[52] U.S. Cl. ............................ 554/52; 554/51; 554/42; 554/66; 554/68; 554/69; 510/119; 510/123; 510/125; 510/135
[58] Field of Search ........................... 554/68, 69, 52, 554/51, 42, 66; 510/119, 123, 125, 135

[56] References Cited

U.S. PATENT DOCUMENTS 2,717,894  9/1955  Schwartz .
5,312,934  5/1994  Letton .

*Primary Examiner*—Deborah D. Carr
*Attorney, Agent, or Firm*—Miles B. Dearth

[57] ABSTRACT

The invention relates to high-foaming zwitterionic and anionic surfactants which are prepared by sulfation of N,N-dialkylaminoalkyl-sugar amides, preferably using gaseous sulfur trioxide. The invention furthermore relates to compositions which comprise known surfactants and suitable solvents, in addition to the novel active compounds. The novel surfactants are particularly suitable for detergents and cosmetic formulations.

7 Claims, No Drawings

SULPHATES OF FATTY-ACID POLYHYDROXYALKYLAMIDES AND THEIR USE

This application is a 371 of PCT/EP97/03266 filed Jun. 21, 1997.

The invention relates to high-foaming sulfates of fatty acid polyhydroxyalkylamides, compositions comprising these sulfates, a process for the preparation of the sulfates and of the compositions and their use.

Organic sulfates which contain long hydrophobic alkyl groups, such as, for example, fatty alcohol sulfates or sulfated fatty alcohol alkoxylates, are active anionic surfactants which have diverse uses.

U.S. Pat. No. 2,717,894 and WO-A 94/12472 describe sulfates of fatty acid polyhydroxyalkylamides. These compounds are prepared by reaction of fatty acid polyhydroxyalkylamides with typical sulfating reagents, such as oleum, gaseous sulfur trioxide, $SO_3$/pyridine complex or chlorosulfonic acid. As stated in U.S. Pat. No. 2,717,894, the sulfated products have a significantly increased foaming power, compared with the neutral amides on which they are based.

It has now been found, surprisingly, that sulfates of amino-functionalized fatty acid polyhydroxyalkylamides which, in the non-neutralized form, are predominantly in the zwitterionic structure (see example) also foam to a considerably greater degree, compared with the nonionic starting amides, and are additionally distinguished by an improved skin tolerance. These novel active compounds are prepared with the aid of the sulfating reagents already mentioned.

The surfactants according to the invention correspond to the following formulae (I) and (II)

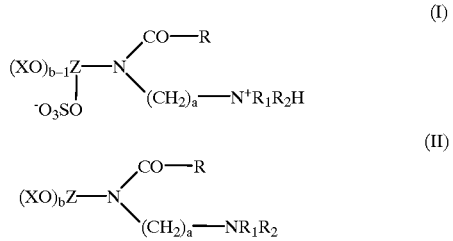

in which
CO—R is an aliphatic acyl radical having 6 to 22 carbon atoms,
$R_1$ and $R_2$ are a $C_1$ to $C_4$-alkyl radical,
a is a number from 2 to 4,
b is a number from 3 to 9 and
$Z(OX)_b$ is an unbranched, aliphatic, partly sulfated polyhydroxyhydrocarbon radical having 4 to 12 carbon atoms in the radical Z, where X is a hydrogen atom or an $SO_3H$ group or an $SO_3M$ group, in which M is one alkali metal or half an alkaline earth metal equivalent or ammonium, with the proviso that X is not hydrogen in one to (b-2) cases.

The sulfates of the formulae (I) and (II) according to the invention, for example the compound 2 described in the example, give very good values in the Ross-Miles foam height test and in the whipped foam volume test in 0.1% strength concentration in water at pH 7. The sulfates according to the formulae (I) and (II) can be combined as desired with cationic, nonionic, amphoteric or anionic surfactants, for example with ether-sulfates based on glycol monoalkyl ethers or alkyl sulfates or alkyl-sulfonates. The sulfates according to the formulae (I) and (II) can also advantageously be used in combination with fatty acid polyhydroxylamides, in particular with the N,N-dialkylaminoalkyl-sugar amides used for their preparation. The surfactants according to the invention dissolve in water, lower alcohols, lower glycols or a mixture of these solvents. The same applies to compositions of the sulfates according to the formulae (I) and (II) with suitable cosurfactants.

The preparation of a suitable dialkylaminopropyl-glucamide according to a process which is already known is first described below. Novel sulfates according to the formulae (I) and (II) are prepared from this precursor in the example.

Preparation of fatty acid polyhydroxyalkylamide $C_{12/14}$-dimethylaminopropyl-glucamide (DMAP-GA):

304.5 g of a 41% strength by weight aqueous solution of a technical grade N-(3-dimethylamino)-propylglucamine (prepared according to U.S. Pat. No. 4,021,539, Example F), called DMAP-G in the following, having a DMAP-G content of 96% by weight, based on the solid substance (i.e. 0.45 mol of DMAP-G), are dewatered with the aid of a customary stripping apparatus. For this purpose, the solution is heated to about 100° C. and initially dewatered under normal pressure up to a residual water content of about 5% by weight. The solution is now heated to 130° C., for further dewatering, and kept at this temperature, a vacuum of up to 25 mbar being applied stepwise. Dewatering is carried out down to a residual water content of 0.2% by weight. 104.1 g (0.473 mol) of $C_{12/14}$-fatty acid methyl ester (molecular weight 220 g/mol, according to the hydrolysis number) are added at 130° C. with stirring to the melt thus obtained. The mixture has a temperature of 120° C. 6.1 g of sodium methylate (30% strength by weight in methanol, 7.5 mol %, based on the DMAP-G) are now also added dropwise in the course of 3 minutes and the reaction mixture is kept at about 100° C. The methanol formed by the reaction is initially left in the system. After about 20 minutes, a clear reaction solution is present. A vacuum of 60 mbar is now applied and a temperature of about 95° C. is established, the reaction mixture further reacting for about 80 minutes, with the methanol being distilled off the solution thus obtained comprises about 90% by weight of $C_{12/14}$-DMAP-GA, based on the solid content.

EXAMPLE

Preparation of $C_{12/14}$-DMAP-GA sulfate (compound 1):

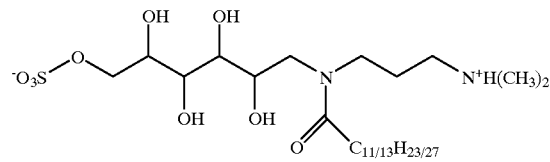

A 90% strength by weight $C_{12/14}$-DMAP-GA-containing reactor mix (preparation as described above) is reacted with an $SO_3$/air mixture comprising 2.2% by volume of $SO_3$ in a molar ratio of 0.98 ($SO_3$:DMAG-GA) in a falling film reactor. The product flowing out, which has a pH of 2.2 (measurement in 1% strength aqueous solution), is removed to an ice-cooled receiver. The content of compound 1 according to the invention is 73.1%.

The sodium salt according to the invention (compound 2) can be obtained by neutralization of compound 1 with aqueous sodium hydroxide solution:

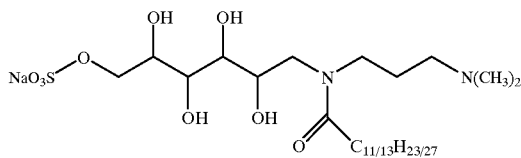

What is claimed is:

1. A high-foaming surfactant which has the following formula (I) or (II)

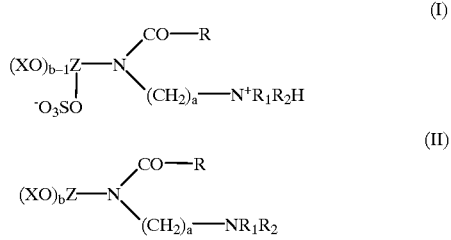

in which
CO—R is an aliphatic acyl radical having 6 to 22 carbon atoms,
$R_1$ and $R_2$ are a $C_1$ to $C_4$-alkyl radical,
a is a number from 2 to 4,
b is a number from 3 to 9 and
$Z(OX)_b$ is an unbranched, aliphatic, partly sulfated polyhydroxyhydrocarbon radical having 4 to 12 carbon atoms in the radical Z, where X is a hydrogen atom or an $SO_3H$ group or an $SO_3M$ group, in which M is one alkali metal or half an alkaline earth metal equivalent or ammonium, with the proviso that X is not hydrogen in one to (b-2) cases.

2. The preparation of a compound of the formula (I) or (II) by reaction of a compound of the following formula

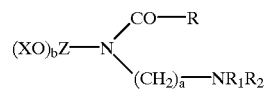

in which R, $R_1$, $R_2$, a and b have the meaning given in claim 1, $Z(OX)_b$ is an unbranched aliphatic polyhydroxyhydrocarbon radical having 4 to 12 carbon atoms in the radical Z and X is hydrogen, with a sulfating reagent from the group consisting of oleum, sulfur trioxide, sulfur trioxide/pyridine complex or chlorosulfonic acid, it being possible for the sulfate of the formula (I) primarily obtained to be converted into the corresponding alkali metal, alkaline earth metal or ammonium salt of the formula (II) by neutralization.

3. The process as claimed in claim 2, wherein gaseous sulfur trioxide is used.

4. A method of use for a compound of the formula (I) or (II) as claimed in claim 1 as an active compound in detergents and cosmetic formulations comprising combining said compound of the formula (I) or (II) together with another cationic, nonionic amphoteric or anionic surfactant, and a solvent, said solvent is selected from the group consisting of water, alcohol, glycol and mixtures thereof.

5. A composition which comprises a content of at least 2% by weight, based on the composition, of at least one compound as claimed in claim 1.

6. A composition as claimed in claim 5, which, in addition to a surfactant as claimed in claim 1, comprises at least one cosurfactant from the group consisting of cationic, nonionic, amphoteric and anionic surfactants.

7. A composition as claimed in claim 5 which comprises at least one solvent from the group consisting of water, lower alcohols, lower glycols and mixtures thereof.

* * * * *